United States Patent
Chuck et al.

(10) Patent No.: US 9,474,487 B2
(45) Date of Patent: Oct. 25, 2016

(54) IMPLANTABLE DEVICES AND METHODS FOR MEASURING INTRAOCULAR, SUBCONJUNCTIVAL OR SUBDERMAL PRESSURE AND/OR ANALYTE CONCENTRATION

(75) Inventors: Roy S. Chuck, Great Neck, NY (US); George Baerveldt, Monarch Beach, CA (US); Jim-Son Chou, Irvine, CA (US)

(73) Assignee: BCC Enterprise, Laguna Hills, CA (US)

( * ) Notice: Subject to any disclaimer, the term of this patent is extended or adjusted under 35 U.S.C. 154(b) by 643 days.

(21) Appl. No.: 13/185,277

(22) Filed: Jul. 18, 2011

(65) Prior Publication Data

US 2012/0041552 A1    Feb. 16, 2012

Related U.S. Application Data

(62) Division of application No. 10/754,479, filed on Jan. 9, 2004, now abandoned.

(60) Provisional application No. 60/439,307, filed on Jan. 9, 2003, provisional application No. 60/439,308, filed on Jan. 9, 2003.

(51) Int. Cl.
*A61B 5/00* (2006.01)
*A61F 2/14* (2006.01)
*A61B 3/16* (2006.01)

(52) U.S. Cl.
CPC ............... *A61B 5/686* (2013.01); *A61B 3/16* (2013.01); *A61B 5/6867* (2013.01); *A61F 2/14* (2013.01)

(58) Field of Classification Search
CPC ...... A61B 3/0008; A61B 3/16; A61B 3/165; A61B 5/03; A61B 5/14555; A61B 5/686; A61B 5/6867; A61F 2/14
See application file for complete search history.

(56) References Cited

U.S. PATENT DOCUMENTS

| | | | |
|---|---|---|---|
| 4,089,329 A | 5/1978 | Couvillon et al. | |
| 4,305,399 A | 12/1981 | Beale | |
| 5,109,852 A | 5/1992 | Kaye et al. | |

(Continued)

OTHER PUBLICATIONS

Peter Walter et al., "Development of a Completely Encapsulated Intraocular Pressure Sensor," Ophthlmic Res 2000; 32: 278-284.

(Continued)

*Primary Examiner* — Howie Matthews
(74) *Attorney, Agent, or Firm* — Robert D. Buyan; Stout, Uxa & Buyan, LLP

(57) ABSTRACT

Methods, apparatus and systems for measuring pressure and/or for quantitative or qualitative measurement of analytes within the eye or elsewhere in the body. Optical pressure sensors and/or optical analyte sensors are implanted in the body and light is cast from an extracorporeal light source, though the cornea, conjunctiva or dermis, and onto a reflective element located within each pressure sensor or analyte sensor. The position or configuration of each sensor's reflective element varies with pressure or analyte concentration. Thus, the reflectance spectra of light reflected by the sensors' reflective elements will vary with changes in pressure or changes in analyte concentration. A spectrometer or other suitable instrument is used to process and analyze the reflectance spectra of the reflected light, thereby obtaining an indication of pressure or analyte concentration adjacent to the sensor(s). The wavelength of the interrogating beam of light may vary to control out potential interference or inaccuracies in the system.

21 Claims, 6 Drawing Sheets

(56) References Cited

U.S. PATENT DOCUMENTS

| | | | |
|---|---|---|---|
| 5,217,015 A | 6/1993 | Kaye et al. | |
| 5,810,005 A * | 9/1998 | Dublin, Jr. | A61B 5/021 600/398 |
| 5,916,179 A * | 6/1999 | Sharrock | 600/587 |
| 6,110,110 A * | 8/2000 | Dublin et al. | 600/405 |
| 6,193,656 B1 * | 2/2001 | Jeffries | A61B 3/16 600/398 |
| 6,210,346 B1 * | 4/2001 | Hall | A61B 5/031 600/561 |
| 6,287,256 B1 | 9/2001 | Park et al. | |
| 6,419,361 B2 | 7/2002 | Cabib et al. | |
| 6,443,893 B1 | 9/2002 | Schnakenberg et al. | |
| 6,517,483 B2 | 2/2003 | Park et al. | |
| 6,595,920 B2 | 7/2003 | Walton | |
| 6,712,764 B2 | 3/2004 | Jeffries et al. | |
| 6,796,942 B1 | 9/2004 | Kreiner et al. | |
| 6,939,299 B1 | 9/2005 | Petersen et al. | |
| 6,976,982 B2 | 12/2005 | Santini, Jr. et al. | |
| 7,131,945 B2 * | 11/2006 | Fink | A61B 3/16 600/398 |
| 7,137,952 B2 | 11/2006 | Leonardi et al. | |
| 7,654,957 B2 * | 2/2010 | Abreu | 600/399 |
| 7,678,065 B2 | 3/2010 | Haffner et al. | |
| 8,142,364 B2 | 3/2012 | Haffner et al. | |
| 2001/0001311 A1 | 5/2001 | Park et al. | |
| 2002/0159671 A1 * | 10/2002 | Boyd | G01D 5/268 385/12 |
| 2003/0078487 A1 | 4/2003 | Jeffries et al. | |
| 2003/0146393 A1 * | 8/2003 | Youngner | G01L 9/0079 250/458.1 |
| 2004/0116794 A1 * | 6/2004 | Fink | A61B 3/16 600/398 |
| 2004/0254438 A1 * | 12/2004 | Chuck | A61B 3/16 600/398 |
| 2005/0159660 A1 * | 7/2005 | Montegrande | A61B 5/0031 600/398 |
| 2007/0112263 A1 * | 5/2007 | Fink | A61B 3/16 600/398 |
| 2007/0123767 A1 * | 5/2007 | Montegrande | A61B 3/16 600/398 |
| 2009/0076367 A1 | 3/2009 | Sit et al. | |
| 2009/0099442 A1 * | 4/2009 | Paden | A61B 3/16 600/398 |
| 2009/0203985 A1 * | 8/2009 | Ehrecke | A61B 3/16 600/398 |

OTHER PUBLICATIONS

Bjorn Svedbergh et al., "The IOP-IOL A Probe Into the Eye," Acta Ophthalmologica, 70 (1992), 266-268.

Carter, Collins C, "Miniature Passive Pressure Transensor for Implanting in the Eye", IEEE Transactions on Bio-Medical Engineering, vol. BME-14, No. 2: 74-83, 1967.

Rosengren, Lars, et al., "A system for passive implantable pressure sensors", Sensors and Actuators A 43:55-58, 1994.

* cited by examiner

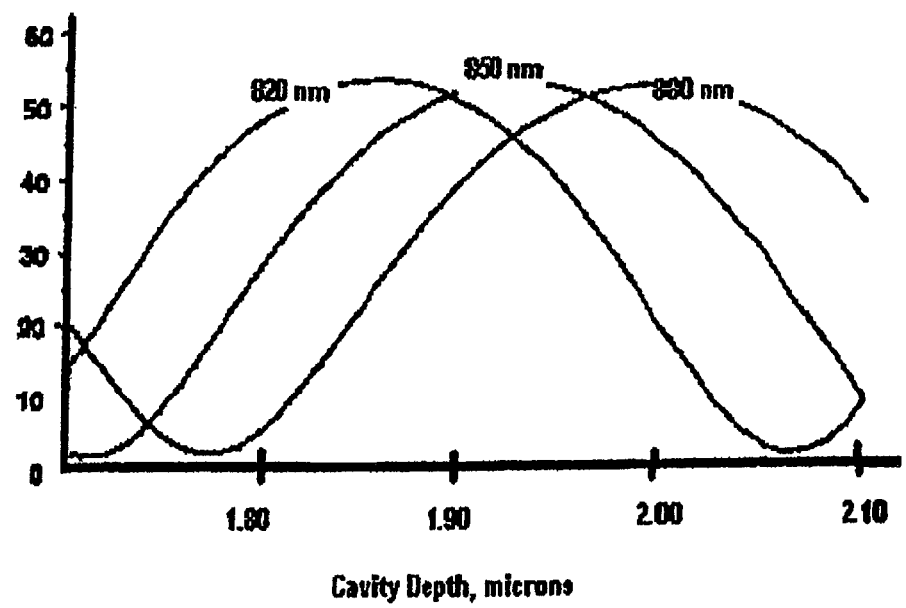
FIG. 4     (PRIOR ART)
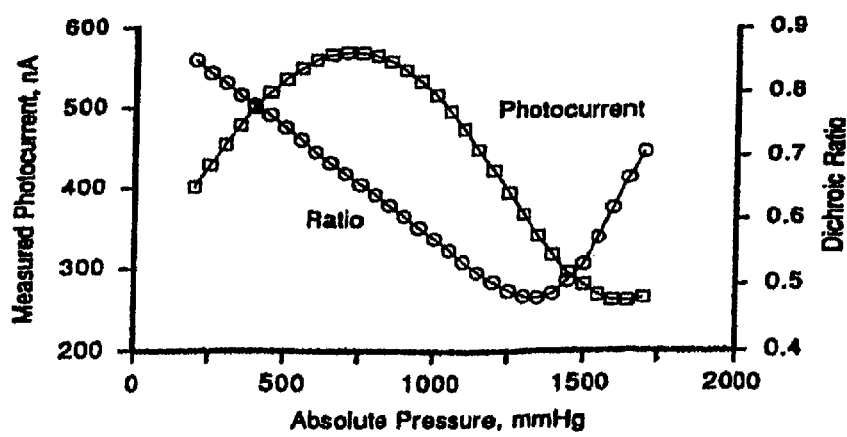
FIG. 5     (PRIOR ART)

IMPLANTABLE DEVICES AND METHODS FOR MEASURING INTRAOCULAR, SUBCONJUNCTIVAL OR SUBDERMAL PRESSURE AND/OR ANALYTE CONCENTRATION

RELATED APPLICATIONS

This application is a division of U.S. patent application Ser. No. 10/754,479 filed Jan. 9, 2004, now abandoned, and which claims the benefit of U.S. Provisional Application Ser. No. 60/439,307 filed Jan. 9, 2003 and 60/439,308 filed Jan. 9, 2003, the entire disclosure of each such prior application being expressly incorporated herein by reference.

BACKGROUND OF THE INVENTION

Measurement of Intraocular Pressure

The term "glaucoma" encompasses a group of diseases, which cause progressive damage to the optic nerve and resultant optical field defects, vision loss and, in some cases, blindness. Typically, glaucoma is frequently, but not always, accompanied by abnormally high intraocular pressure.

There are three basic types of glaucoma—primary, secondary and congenital. The most common type of glaucoma is primary glaucoma. Cases of primary glaucoma can be classified as either open angle or closed angle.

Secondary glaucoma occurs as a complication of a variety of other conditions, such as injury, inflammation, vascular disease and diabetes.

Congenital glaucoma is elevated eye pressure present at birth due to a developmental defect in the eye's drainage mechanism.

Glaucoma is the third most common cause of blindness in the United States. Whether it is an increase in the intraocular pressure that causes damage to the retina or an increased susceptibility to damage that may result in an increase in intraocular pressure, titrating the intraocular pressure with careful monitoring is the mainstay of treatment and constitutes an important component in the overall clinical management of the disease.

The etiology of vision loss in glaucoma patients may be due, at least in part, to compression of the vasculature of the retina and optic nerve as a result of increased intraocular pressure. Indeed, it is generally accepted that controlling intraocular pressure through the use of drugs and/or surgery markedly reduces glaucomatous progression in normal-tension glaucoma and decreasing intraocular pressure virtually halts it in primary open-angle glaucoma. Furthermore, it is generally acknowledged that lowering intraocular pressure in glaucoma patients can prevent or lessen the irreversible glaucoma-associated destruction of optic nerve fibers and the resultant irreversible vision loss.

Thus, irrespective of the particular type of glaucoma a patient suffers from, it is typically desirable to obtain periodic measurements of intraocular pressure in order to assess the clinical progression of the disease and/or the efficacy of the treatments being administered. Also, because early diagnosis is important in effectively treating glaucoma, it is also desirable to periodically measure intraocular pressure in patients who do not presently suffer from glaucoma but who may be at risk to contract one of the various types of glaucoma.

Today, intraocular pressure is commonly measured by indirect methods (e.g., pressing a strain gage against the cornea and measuring the depth of corneal depression) or by non-contact methods (e.g., expelling a puff of air against the outer surface of the cornea and measuring the depth of corneal depression). As convenient as these measurements may be, they are inherently inaccurate, mainly because of the error imparted by the varying mechanical properties of the cornea. It has been shown that such indirect intraocular pressure measurements are dependent upon, among other factors, corneal thickness, curvature and rigidity. These factors can vary greatly from individual to individual, and thus gross errors in intraocular pressure estimation are common. These errors can easily result in the misdiagnosis of a glaucomatous or non-glaucomatous state. Moreover, with the advent of corneal refractive surgery, 1.8 million of which were performed in the U.S. last year, measurement of intraocular pressure via indirect methods through the cornea is even more inaccurate secondary to the biomechanical alterations of the cornea caused by surgery. Thus there is a great national and international need to develop a more accurate direct intraocular pressure sensor.

In the past, there have been numerous attempts to construct an accurate, small and safe intraocular pressure sensor. Among the devices proposed were direct cannulation of the anterior chamber of the eye coupled to an extraocular direct pressure monitor, and telemetric units using piezoresistive and acousto-optic elements. Such devices would be implanted in the anterior chamber either as free-standing units, or incorporated as parts of plastic intraocular lenses. The telemetric machines would transfer intraocular pressure readings to external monitoring devices non-invasively through the intact cornea. Although those previously proposed telemetric devices offer potential advantages over their invasive counterparts and the current indirect corneal devices, they still suffer many drawbacks including bulk, need for electrical power and unacceptable signal-to-noise ratios.

Recently, intracavity pressure sensors (e.g. brain and intravascular space) based upon the Fabry-Perot interferometer, in which two parallel, minimally separated, partially reflecting surfaces form an optical reflecting cavity, have been proposed. If one of the parallel surfaces is a pressure-sensitive diaphragm, changes in external pressure cause a change in the depth of the optical reflecting cavity, which in turn alters optical cavity reflectance spectra. Because brain and intravascular elements are optically opaque, current use requires a single wavelength light-emitting diode physically coupled to an input and read-out fiber optic. Alternatively, for the purposes of this current invention, we recognize that the anterior chamber and cornea are optically clear. Thus the input optical wavelengths and reflected output can be detected externally through intact and optically clear anterior chamber and cornea media after intraocular implantation of such a chip-based pressure sensor, either as an independent device or as part of an intraocular lens. In this case, because we are not restricted by the spectral bandpass of an optical fiber, almost any light source, including various LEDs, lasers or white light emitters (filtered and unfiltered) may be used. Moreover, currently available sensors should prove small enough for practical intraocular implantation. The advantages of direct intraocular pressure sensing, no need for electrical power, non-invasive external monitoring, compact chip-based device and optical sensing with high signal-to-noise ratio have been realized in this invention.

Measurement of Intraocular, Subconjunctival or Subdermal Analyte Concentrations

In clinical medicine, it is sometimes desirable to measure the concentration of glucose and/or other analytes within the eye or at other locations within the body, in order to diagnose and/or monitor various conditions including, but not limited to, metabolic or endocrine disorders such as such as diabetes mellitus. Various methods including direct analytical sampling and various forms of spectroscopy have been proposed in the past. Frequent direct invasive sampling, especially from the intraocular and intravascular spaces, has obvious problems. Non-invasive spectroscopic monitoring through skin and intravascular elements has sensitivity and specificity problems associated with both the optical opacity and turbidity of these media and the narrow (but often overlapping) spectroscopic chemical bands of each individual analyte.

Recently biomembranes permeable to specific analytes (e.g. glucose) have been developed. Sensors for these selected compounds usually incorporate direct spectroscopic detection or transduced increased pressure associated with increasing concentrations of the chemical. Such methods either involve invasive sampling of the sample chamber or electrical-powered piezoresistive signal transduction and read-out, all serious drawbacks of the proposed methods.

There remains a need in the art for the development of new devices and methods for measurement of intraocular pressure and/or measurement of intraocular, subconjunctival or subdermal analyte concentration.

SUMMARY OF THE INVENTION

The present invention provides implantable devices, systems and methods for measuring intraocular pressure and/or intraocular, subconjunctival or subdermal analyte concentration(s).

In accordance with the invention, there is provided an intraocular pressure measuring system that comprises a) an implantable optical pressure sensor sized for implantation within the eye, said optical pressure sensor comprising an optical reflecting element which varies relative to changes in intraocular pressure, b) a light source useable to pass light through the cornea of the eye such that the light will strike and be reflected by the optical reflecting element and c) a receiver/processor which receives light which has reflected from the optical reflecting element and processes such reflected light so as to obtain an indication of intraocular pressure. The optical pressure sensor may comprise a Fabry-Perot interferometer. Such optical pressure sensor may be constructed for implantation as stand-alone device or it may be attached to or otherwise associated with a support (e.g., a support member, housing, substrate or other structure) that holds the optical pressure sensor in a substantially fixed (e.g., substantially stationary) position within the eye. Such support may hold the optical pressure sensor at a desired location within the eye where intraocular pressure may be sensed (e.g., within the anterior chamber, posterior chamber or lens capsule). In some embodiments, the support may comprise an intraocular lens assembly having an optic portion and a haptic portion. The optical pressure sensor may be attached to (e.g., mounted on, embedded in or otherwise connected to) the optic portion and/or the haptic portion of such intraocular lens assembly. The optic portion may or may not be configured to perform a refractive vision correcting function. In other embodiments, the support may be in the form of a tubular shunt that is implantable in the eye to facilitate drainage of the drain aqueous humor in glaucoma patients and the optical pressure sensor may be attached to a portion of the shunt that protrudes into the anterior chamber of the eye. In other embodiments, the support may comprise an implantable prosthetic lens that is useable to replace a native ophthalmic lens that has been removed from the patient's eye (e.g., a cataract that has been surgically removed) and the optical pressure sensor may be attached to such prosthetic lens. The support may be configured to perform other secondary functions or it may be configured to function solely as a support for the optical pressure sensor without performing any secondary function(s). The light source may comprise an LED or other light emitting apparatus that emits light of a desired wavelength (e.g., white light). The optical pressure sensor may be positioned at a location within the eye whereby light from the light source will pass inwardly through the cornea of the patient's eye, strike and be reflected by the reflective element of the optical pressure sensor. The reflected light will then pass outwardly through the cornea and will be received and processed by the receiver/processor. Because the optical pressure sensor moves in response to changes in intraocular pressure, the wavelength of the reflected light also changes in accordance with such changes in intraocular pressure. Thus, the receiver may be a lens, mirror or any other single or multiple light receiving or light channeling apparatus. The processor may be a spectrometer or any other apparatus that measures or detects changes in the wavelength of the reflected light received by the receiver. The receiver/processor may comprise an integrated, single assembly that incorporates both the receiver and processor. Alternatively, the receiver/processor may comprise a receiver that is separate from and not physically connected to the processor.

Further in accordance with the invention, there is provided a system for for intraocular, subconjunctival or subdermal determination of one or more analytes (e.g., chemical substances). Such analyte determination system generally comprises a) an optical analyte sensor sized for intraocular, subconjunctival or subdermal implantation, said optical sensor comprising an optical reflecting element which varies relative to changes in the amount or concentration of the analyte, b) a light source useable to pass light through the cornea, conjunctiva or skin such that the light will strike and be reflected by the optical reflecting element of the optical sensor and c) a receiver/processor which receives light that has reflected from the optical reflecting element and processes such reflected light to obtain a qualitative or quantitative determination of the analyte. The analyte may be a substance that occurs naturally within the body (e.g., glucose, certain enzymes, hormones, etc.) or a substance that has accumulated in or entered the body (e.g., certain drugs or toxins of exogenous origin). As used herein the terms "subconjunctival" and "subdermal" refer to locations beneath at least the upper surface of the conjunctiva or skin and, thus, are to be construed to include locations within the conjunctiva or skin as well as locations that are entirely beneath the conjunctiva or skin. The optical reflective element of the optical analyte sensor may move in response to changes in the osmolar pressure, osmolarity and/or osmolality (collectively "osmolar changes") of a body fluid that result from changes in the concentration of the analyte within that body fluid. In this regard, the optical analyte sensor may comprise a closed chamber that is at least partially closed by a permeable or, more typically, a semipermeable membrane. As osmolar changes occur in the body fluid adjacent to the semipermeable membrane, fluid will diffuse into or out of the chamber, through the semipermeable membrane. Such diffusion of fluid into or out of the chamber will result in upward or downward movement of the reflective member in response to the osmolar changes in the adjacent body fluid. This results in changes in the wavelength of the light reflected by the reflective member. Such changes in wavelength are detected by the receiver/processor and the presence or concentration of the analyte in that body fluid is determined on the basis of such changes in wavelength of the reflected light. Thus, as in the above-described pressure sensor, the receiver may be a lens, mirror or any other single or multiple light-receiving or light-channeling apparatus. The processor may be a spectrometer or any other apparatus that measures or detects changes in the wavelength of the reflected light received by the receiver. The receiver/processor may comprise an integrated, single assembly that incorporates both the receiver and processor. Alternatively, the receiver/processor may comprise a receiver that is separate from and not physically connected to the processor. The optical analyte sensor may be constructed for implantation as stand-alone device or it may be attached to or otherwise associated with a support (e.g., a support member, housing, substrate or other structure) that holds the optical analyte sensor in a substantially fixed (e.g., substantially stationary) intraocular, subconjunctival or subdermal location. Any of the support types described above with respect to the optical pressure sensor may also be used with this optical analyte sensor. Additionally, various other types of functional supports may be used in subconjunctival or subdermal applications of the device (e.g., the optical analyte sensor may be mounted on a drug delivery implant or other medical device that is implanted within or beneath the skin).

Still further in accordance with the invention, the optical pressure sensor and the optical analyte sensor may be used in combination. In this regard, the optical pressure sensor and the optical analyte sensor may be mounted on a common support, of the types described herein. In such embodiments wherein the optical pressure sensor and the optical analyte sensor are used in combination, a single light source or separate light sources, may be used to cast light on the optical pressure sensor and the optical analyte sensor. In embodiments where a single light source is used, such single light source may be adjustable to vary the direction, wavelength and/or other characteristics of the of the light beam that emanates from the light source, thereby facilitating its use for both applications. Also, a single receiver/processor or separate receiver processors. may be used to receive and process the light reflected from the optical pressure sensor and optical analyte sensor. In embodiments where a single receiver/processor is used, such single receiver/processor may be adjustable to vary the direction from which the reflected light is received and/or the particular characteristic(s) of the reflected light that are processed by the processor.

Still further in accordance with the invention, there are provided methods for measuring or determining intraocular pressure and/or intraocular, subdermal or subconjunctival analyte concentration using the devices and systems summarized above.

Further aspects, elements, embodiments and details of the invention will be apparent to those of skill in the art upon reading of the detailed description and examples provided herebelow.

BRIEF DESCRIPTION OF THE DRAWINGS

FIGS. 4-7 are previously published graphs showing the linearity and accuracy of Fabry-Perot interferometers of the type used in the present invention.

DETAILED DESCRIPTION AND EXAMPLES

Recently intracavity pressure sensors (e.g. brain and intravascular space) based upon the Fabry-Perot interferometer, in which two parallel, minimally separated, partially reflecting surfaces form an optical reflecting cavity, have been proposed. If one of the parallel surfaces is a pressure-sensitive diaphragm, changes in external pressure cause a change in the depth of the optical reflecting cavity, which in turn alters optical cavity reflectance spectra. Because brain and intravascular elements are optically opaque, current use requires that a single wavelength light-emitting diode be physically coupled to an input and read-out fiber optic. In contrast, for the purposes of the current invention, the cornea and conjunctiva are optically clear and that the dermis poses no optical obstruction to various defined wavelengths of light (or the dermis may be treated with one of more chemical agents to minimize the light scattering properties of the dermis). Thus the input optical wavelengths and reflected output from the optical pressure sensors and optical analyte sensors of the present invention can be detected externally through intact corneal, conjunctival and dermal media and will not be restricted by the spectral bandpass of an optical fiber and because of the optical clarity of these structures. Also, in the systems of the present invention, almost any light source, including various LEDs, lasers or white light emitters (filtered and unfiltered) may be used (in the case of skin, the dermis must be transparent to the wavelengths). The advantages of direct pressure sensing and/or analyte determination systems of the present invention include; the lack of any need for electrical power to the implant, the capability of non-invasive external monitoring, and a comparatively high signal-to-noise ratio have been realized in this invention.

Figure 8:
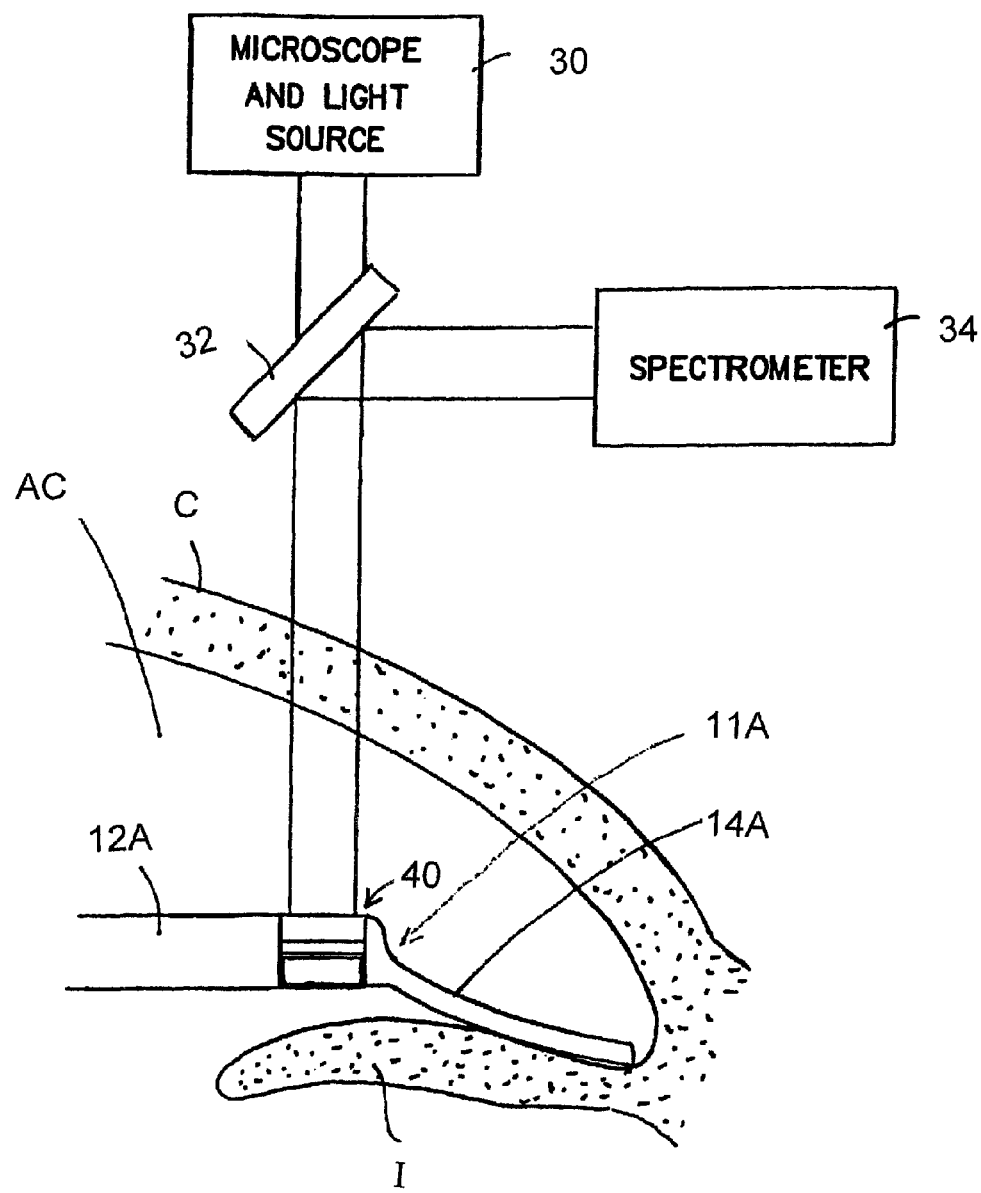
FIG. 8 is a schematic diagram of a analyte sensing system of the present invention comprising an implantable analyte sensor implanted within the anterior chamber of a human eye in combination with an extracorporeal microscope/light source and an extracorporeal spectrometer.
Figures 9A, 9B:
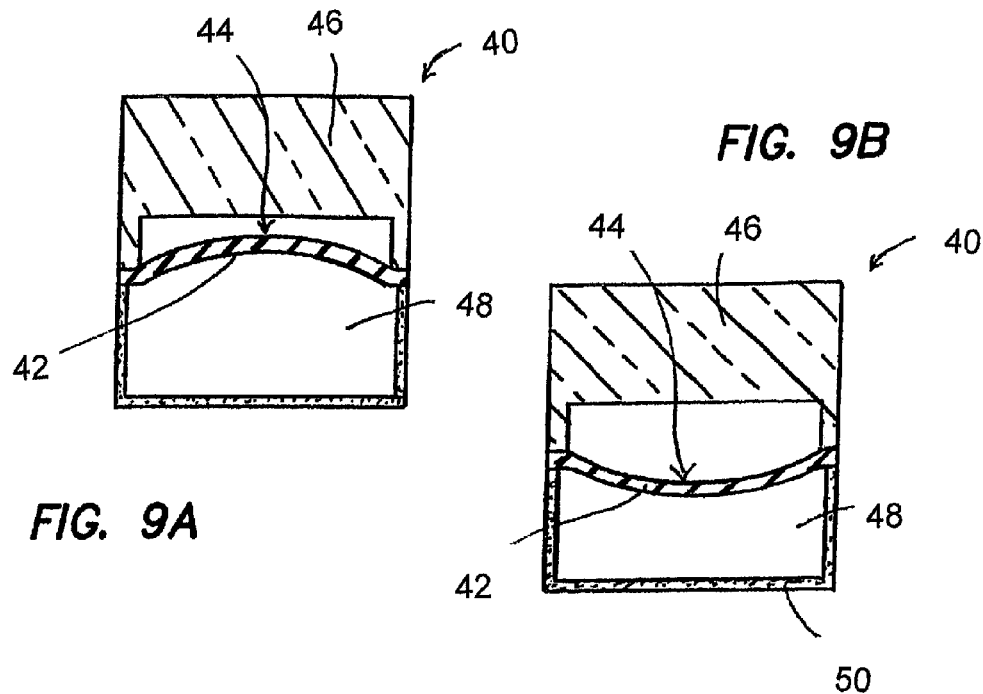
FIG. 9A is a cross sectional view of the implantable analyte sensor device of FIG. 8 with its diaphragm positioned in response to a high concentration of analyte in the aqueous humor of the eye.
FIG. 9B is a cross sectional view of the implantable analyte sensor device of FIG. 8 with its diaphragm positioned in response to a low concentration of analyte in the aqueous humor of the eye.
Figure 10:
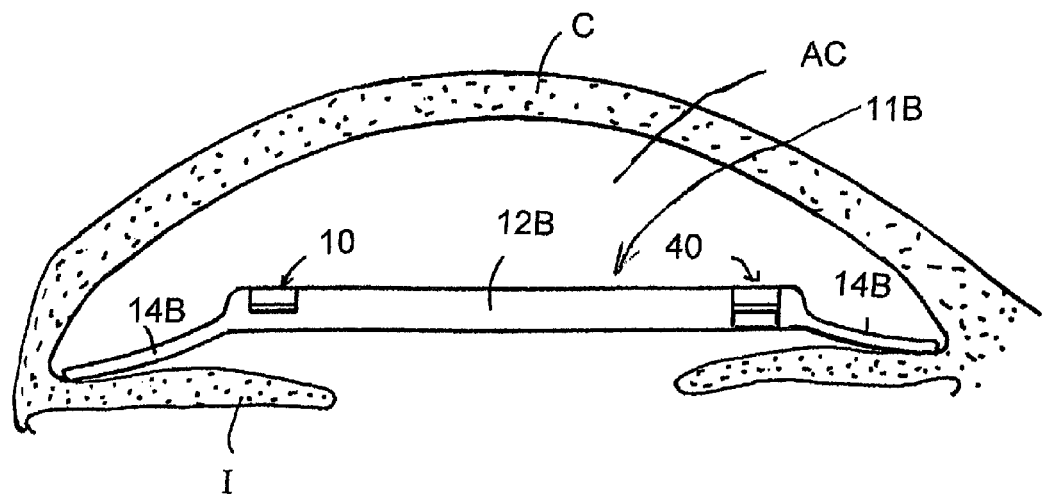
FIG. 10 shows another embodiment of the present invention wherein both the optical pressure sensor and optical analyte sensor are attached to a common support that comprises an intraocular lens assembly implanted in the anterior chamber of a patient's eye.

As described in detail herebelow, FIGS. 1-7 relate to one particular non-limiting example of an intraocular pressure sensing system of the present invention, FIGS. 8-9b relate to one particular non-limiting example of an intraocular analyte determining system of the present invention and FIG. 10 relates to one particular non-limiting example of an intraocular pressure sensing and analyte determining system of the present invention. Several of these figures depict anatomical structures of the human eye. Such anatomical structures are labeled as follows:

| | |
|---|---|
| AC | Anterior Chamber |
| C | Cornea |
| I | Iris |
| P | Pupil |
| L | Native Lens |

Example 1

Intraocular Pressure Sensing System

An intraocular pressure sensing system of the present invention is shown in FIGS. 1-3b. As may be seen in FIG. 1, an optical pressure sensor 10 is mounted on a support 11. This support 11 comprises a haptic 14 and an optic 12, in the nature of a typical phakic intraocular lens adapted for implantation within the anterior chamber AC of the eye. In the embodiment shown, the optical pressure sensor 10 is attached to one edge of the optic 12, but it is to be appreciated that the optical pressure sensor could also be attached to the optic 12 and/or haptic 14 at other locations or in other ways. The optic may or may not provide some refractive vision correction in addition to performing the function of a support 11 for the optical pressure sensor 10. On example of a 2-piece phakic intraocular lens that may be used to form the support 11 is the Kelman Duet Implant manufactured by TEKIA, Inc., Irvine, Calif.

The support 11 holds the optical pressure sensor 10 at a substantially fixed (e.g., substantially stationary) position within the anterior chamber AC such that the pressure sensor 10 will sense changes in the aqueous humor that fills the anterior chamber. Such pressure of the aqueous humor typically becomes abnormally high in patients who suffer from glaucoma and, thus, this embodiment of the invention is useable to monitor disease progression and/or treatment efficacy in glaucoma patients.

Figure 3A:
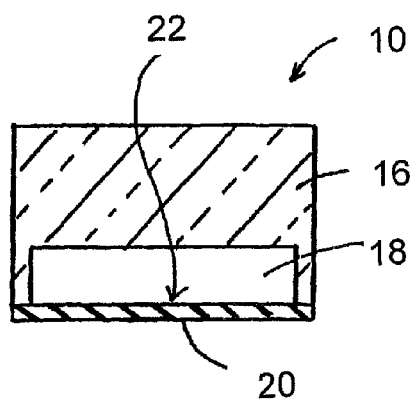
FIG. 3A is a cross sectional view of the implantable pressure sensor device of FIG. 1 with its diaphragm positioned in response to a low intraocular pressure.
Figure 3B:
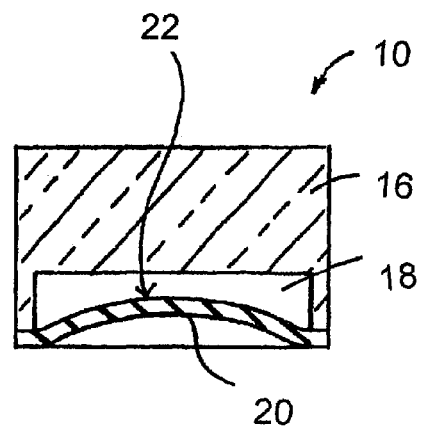
FIG. 3B is a cross sectional view of the implantable pressure sensor device of FIG. 1 with its diaphragm positioned in response to a high intraocular pressure.

FIGS. 3a and 3b show details of the intraocular pressure sensor 10. As shown, this intraocular pressure sensor 10 comprises a translucent body 16 (or alternatively an opaque body having a translucent window formed therein) with an optical reflecting cavity 18 formed at one end thereof. A flexible diaphragm 20 forms the bottom wall of such cavity 18. A reflective surface 22 is formed on the upper surface of the diaphragm 20. A separate reflective surface may also be formed on the wall of the cavity 18 that is opposed to the reflective surface 22 of the diaphragm 20. The optical pressure sensor 10 is positioned in the anterior chamber AC such that the underside of the outer surface of the diaphragm 20 is in contact with the aqueous humor that fills the anterior chamber AC. When the intraocular pressure is normal, the force exerted on the diaphragm 20 by the aqueous humor will allow the diaphragm 20 to substantially remain in a first position, as shown in FIG. 3A. However, as the intraocular pressure increases, the diaphragm 20 will progressively move upwardly, as shown in FIG. 3B.

The optical pressure sensor 10 may be a miniaturized Fabry-Perot interferometer in which two parallel, minimally separated, partially reflecting surfaces form an optical reflecting cavity which is commercially available as Model 20 and Model 60, from RJC Enterprises, Woodinville, Wash.

The size of the optical pressure sensor is about 300 µm×300 µm with about 200 µm depth. One of the parallel surfaces 22 is a surface of the pressure-sensitive diaphragm 20 that changes position with changes in external pressure. This results in a change in the depth of the optical reflecting cavity 18 and a resultant change in the reflectance spectra. Thus, the changes in the reflectance spectra correlate with changes in depth of the reflecting cavity 18 and, thus, also correlates to changes in the pressure of the aqueous humor in the other side of the diaphragm 20.

Figure 2:
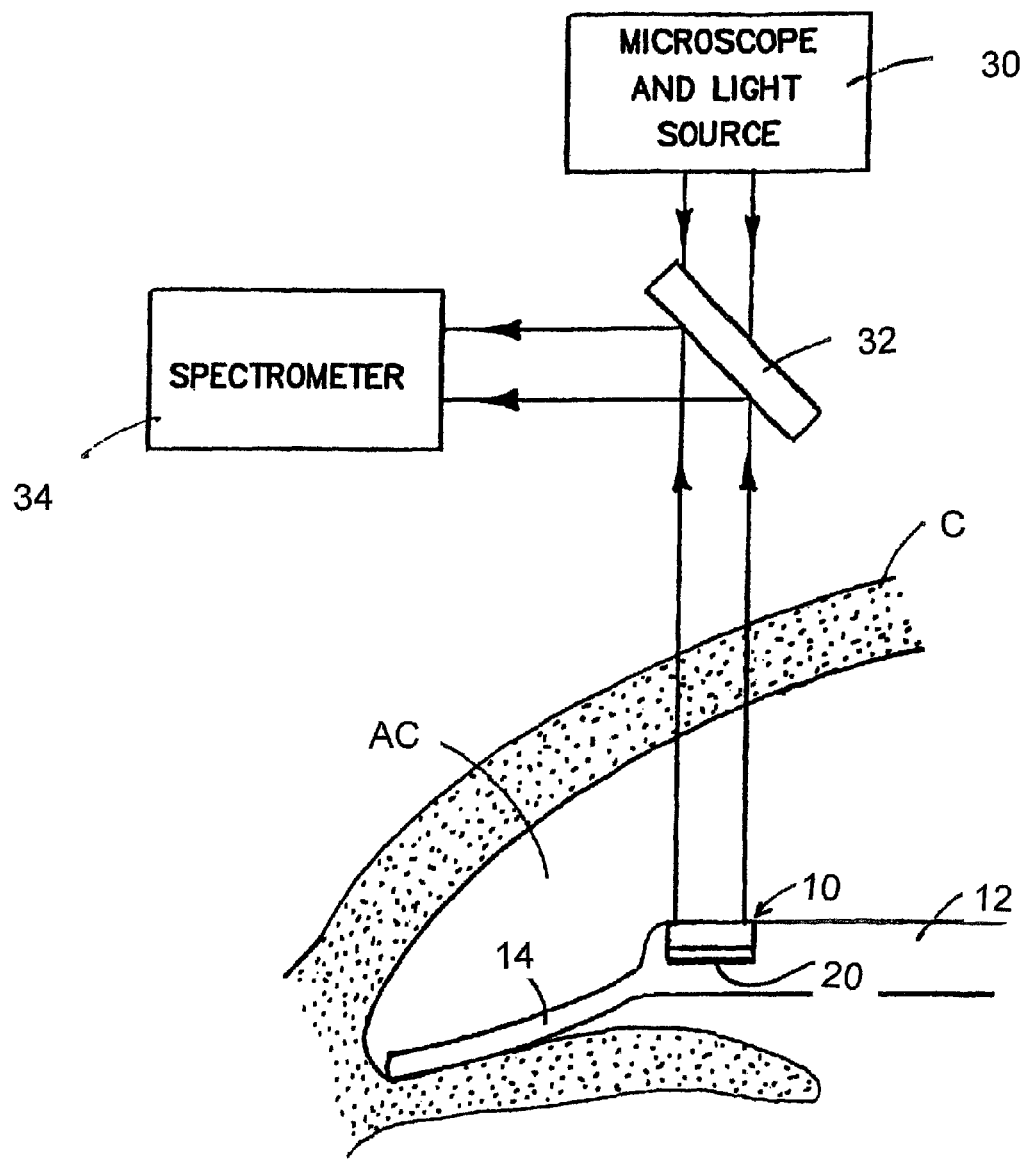
FIG. 2 is a schematic diagram of a pressure sensing system of the present invention, including the implantable pressure sensor device of FIG. 1 in combination with an extracorporeallly positioned microscope/light source and an extracorporeallly positioned spectrophotometer.
Figure 6:
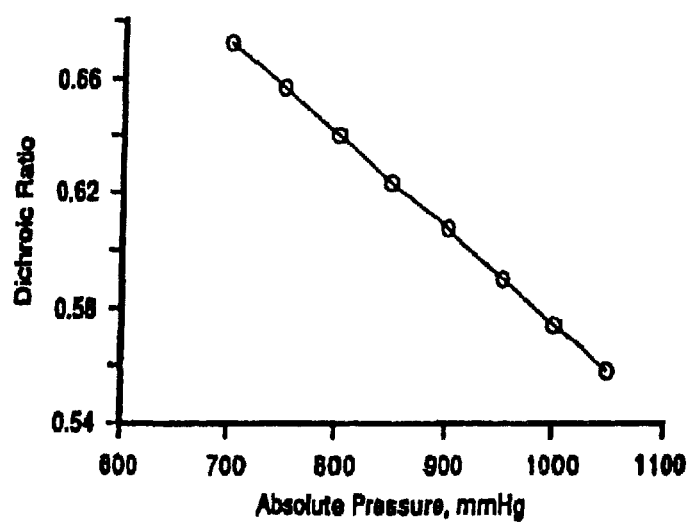
Figure 7:
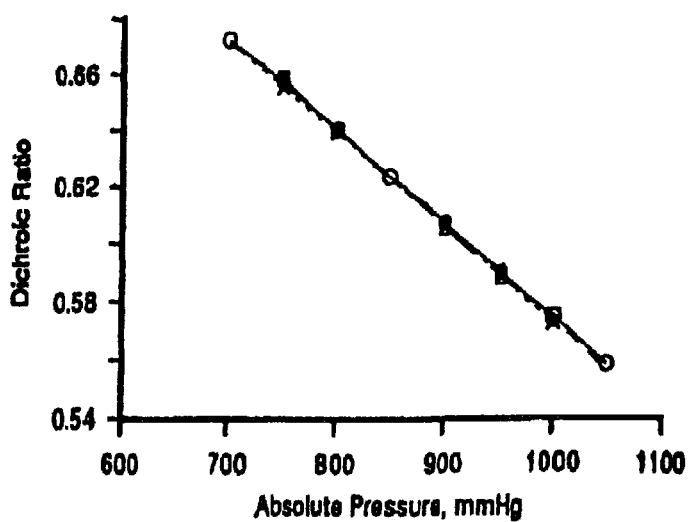

FIG. 2 illustrates the manner in which intraocular pressure is read from the implanted optical pressure sensor 10. A light source 30 is positioned in front of the patient's eye. A beam of light is cast from the light source 30, through the cornea C of the eye, though the translucent body (or window) of the sensor 10 and upon the reflective surface 22 of the diaphragm 20. This light is then reflected from the reflective surface 22, outwardly through the cornea C and is received by a receiver 32 such as a mirror, lens, waveguide or other light directing member. The reflected light is directed by the receiver 32 to a processor 34, such as a spectrometer, which then processes the reflected light in a manner that determines a parameter of the reflected light that is dependent upon the depth of the reflecting cavity 18 and, thus, can be used to calculate the pressure of the fluid exerted against the pressure sensitive diaphragm 20.

The processor 34 may be a reflectance spectrum analyzer that measures the difference in reflected light emanating from the optical sensor 10 at different wavelengths. The reflectance of the optical sensor 10 is not only dependent on the depth of the reflecting cavity 18 cavity and thus on the pressure, but is also dependent on the wavelength of the light that is transmitted against the reflecting surface 22 of the diaphragm 20 from the light source 30. In this regard, FIG. 4 (excerpted from Wolthius et al.) shows the relationship between the depth of the reflecting cavity 18 and reflectance determined by the processor 34 when the light source 30 emits light at wavelengths of 820, 850 and 880 nm. By determining the ratio of the reflectance of different wavelengths, the signal to noise ratio can be improved and the linearity range can be extended, as demonstrated in FIG. 5 and the following equation:

$\Delta = \pi(\lambda_C - \lambda_{C'})/2\omega$ where $\omega$ is the spectral width of the light source, $\lambda_C$, $\lambda_{C'}$, are the wavelengths of the two probing light sources $K=(1-R')2/2R'$ where $R'$ is the mean reflectance of the surfaces Ratio=$\frac{1}{2}+2/\pi[(1-K)\sin \Delta'/2K-(1-K)\cos \Delta']$ FIG. 5 shows the total sensor reflectance (measured photocurrent) and the output from dichroic ratio signal analysis (dichroic ratio) plotted with respect to optical cavity depth (absolute pressure), as measure over part of a reflectance cycle. (Excerpt from Wolthuis et. al).

Thus, by using this ratiometric technique the intraocular pressure measuring system of the present invention is insensitive to source intensity and coupling efficiency. In this regard, this type of optical pressure sensor 10 has been coupled to a fiber optic/LED/dicrotic mirror/photodiode system manufactured by Integra Neurosciences, San Diego, Calif. to measure pressure. Figurers 6 and 7 (excerpted from Wolthius et al.) demonstrate the linearity and reproducibility of the measurements obtainable from this type of sensor 10.

Figure 1:
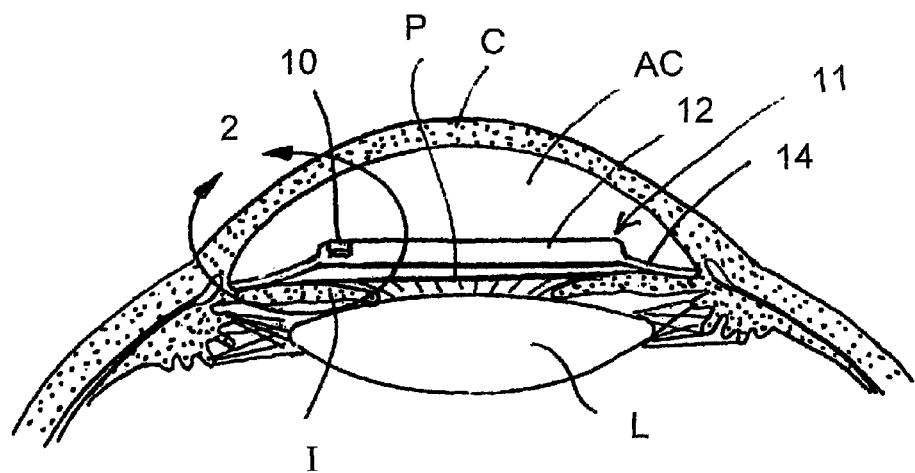
FIG. 1 is a partial, cross-sectional view of a human eye having an implantable pressure sensor device of the present invention implanted within the anterior chamber of the eye.

Although FIGS. 1 and 2 show the optical sensor 10 positioned in the anterior chamber AC of the eye, it will be appreciated that this optical sensor 10 may be positioned anywhere in the eye where intraocular pressure may be measured. For example, the sensor 10 may be positioned in the posterior chamber of the eye. Such positioning of the sensor 10 within the posterior chamber of the eye may be accomplished by removing all or a portion of the vireous humor using known vitrectomy techniques and then placing the sensor 10 (with or without an appropriately configured support 11) within the posterior chamber at a location where light may pass through the cornea, through the pupil and be reflected from the reflective surface 22 of the diaphragm 20. In another example, in a patient who's native lens has been removed due to cataracts or some other pathology, a prosthetic lens may be implanted in place of the previously removed native lens and the sensor 10 may be attached that prosthetic lens implant. Also, it is to be appreciated that various other types of supports 11 may be used. In some instances, the support 11 may be a structure which functions only to support the sensor 10. In other instances, the support may perform some secondary function is addition to holding of the sensor 10. For example, in embodiments where the support 11 is a phakic intraocular lens, the phakic intraocular lens may be constructed to provide some refractive vision correction in addition to holding of the sensor 10. In other instances, in patients who suffer from glaucoma, a shunt may be surgically implanted to facilitate drainage of aqueous humor and resultant lowering of intraocular pressure. Such shunts are typically tubular and one end of the shunt typically protrudes into the anterior chamber AC of the eye. Thus, the optical sensor 10 may be attached to such a shunt (e.g., to the portion of the shunt that resides in the anterior chamber of the eye) such that the shunt will perform the dual function of draining aqueous humor and holding the sensor 10 at a desired location within the eye.

Example 2

Intraocular Analyte Determining System

FIGS. 8, 9A and 9B show a system for quantitative or qualitative determination of an analyte within the eye of a human or veterinary patient. This system comprises an optical analyte sensor 40 that is implanted within the eye. This optical analyte sensor 40 may be configured for implantation as a stand alone device or may be attached to a support 11A. In the particular embodiment shown, the support 11A comprises an intraocular lens system that comprises an optic 12a and a haptic 14a, of the same type as described hereabove in reference to FIG. 2.

The optical analyte sensor 40 is shown in detail in FIGS. 9A and 9B. As shown, the optical analyte sensor 40 comprises a translucent body 46 (or an opaque body having a translucent window) having a hollow cavity 48 formed at one end thereof. One or more walls of the cavity 48, or at least a portion of one wall of the cavity 48, is/are formed of a semipermeable membrane 50 through which a particular analyte (e.g., glucose or some other endogenous substance, a drug, a metabolite, a toxin, etc) will pass. In the embodiment shown, a flexible diaphragm 42 having a reflective surface 44 is mounted transversely within the cavity 48. As the concentration of the analyte increases in the body fluid adjacent to the outer surface of the semipermeable membrane 50, the analyte will diffuse through the semipermeable membrane 50 and into the cavity 48. Some quantity of water may also diffuse into the cavity 48 along with the analyte. This results in an increase in pressure on the diaphragm 42 and will cause the diaphragm to move as shown in FIG. 9A. When the concentration of the analyte in the body fluid decreases, analyte (and possibly water) will diffuse out of the cavity 48, thereby decreasing the pressure on the diaphragm and causing the diaphragm 42 to move in the opposite direction, as shown in FIG. 9B. It will be appreciated that as an alternative to positioning of the diaphragm 42 within the cavity 48, the semipermeable membrane may either abut the pressure-sensitive interferometric cavity, or the membrane may itself serve as the pressure-sensitive diaphragm of the interferometer. The ability to measure concentrations of analytes by these optical analyte sensors 40 may be quite sensitive.

In some embodiments of this invention, chemicals that either react or interact with specific analytes may be placed in the cavity 48. Changes such as altered optical spectroscopic (direct sensing) or volumetric properties (pressure transduction) may then be detected. In this case the semipermeable membrane could be fairly non-selective. The membrane 50 may be any suitable type of membrane that will allow measurement of the analyte(s) of interest. Biomembranes permeable to specific analytes (e.g. glucose) have been developed (e.g., UPE Membrane, Millipore, Bedford, Mass.). Selectively permeable membranes may be used for different analytes, including glucose.

The concentration of the analyte is read using a light source 30, receiver 32 and processor (e.g., a spectrometer) 34 in the same manner as described hereabove with respect to the optical pressure sensor 10.

Example 3

Combined System for Measuring Intraocular Pressure and Analyte Concentration

FIG. 10 shows another embodiment of the present invention wherein both the optical pressure sensor 10 and optical analyte sensor 40 are attached to a common support 11B that comprises an intraocular lens assembly implanted in the anterior chamber Ac of a patient's eye. The support includes an optic 12b and haptic 14c which may be the same as those described above with respect to FIG. 2.

In this embodiment wherein the optical pressure sensor 10 and the optical analyte sensor 40 are used in combination, a single light source 30 or separate light sources 30, may be used to cast light on the reflective surfaces 22 and 44 of the optical pressure sensor diaphragm 20 and the optical analyte sensor diaphragm 40, respectively. In embodiments where a single light source is used, such single light source may be adjustable to vary the direction, wavelength and/or other characteristics of the of the light beam that emanates from the light source, thereby facilitating its use for both applications. Also, a single receiver/processor 34 or separate receiver processors 34. May be used to receive and process the light reflected from the reflective surfaces 22 and 22. In embodiments where a single receiver/processor is used, such single receiver/processor may be adjustable to vary the direction from which the reflected light is received and/or the particular characteristic(s) of the reflected light that are processed by the processor.

Although the invention has been described above with respect to certain embodiments and examples, it is to be appreciated that such embodiments and examples are non-limiting and are not purported to define all embodiments and examples of the invention. Indeed, those of skill in the art will recognize that various modifications may be made to the above-described embodiments and examples without departing from the intended spirit and scope of the invention and it is intended that all such modifications be included within the scope of the following claims.

What is claimed is:

1. A method of determining intraocular pressure in a human or veterinary patient, said method comprising the steps of:
   (A) implanting within the eye an optical pressure sensor that comprises a Fabry-Perot interferometer having two parallel optical reflecting surfaces with an optical reflecting cavity therebetween, wherein one of the optical reflecting surfaces comprises a pressure-sensitive diaphragm that is in contact with intraocular fluid such that the pressure-sensitive diaphragm moves relative to changes in the intraocular pressure of the eye thereby causing the depth of the optical reflecting cavity to vary relative to changes in the intraocular pressure;
   (B) positioning a receiver/processor, which comprises an optical spectrum analyzer, at a location in front of the eye;
   (C) using a light source to cast emitted light at a plurality of wavelengths through the intact cornea of the eye such that the emitted light enters the optical reflecting cavity and reflected light then reflects from the optical reflecting cavity and travels, free of any waveguide, outwardly through the intact cornea and to the receiver/processor positioned in front of the eye; and,
   (D) using the optical spectrum analyzer to ratiometrically measure reflectance spectra of the reflected light at said plurality of wavelengths and to obtain, on the basis of said ratiometric measurement, an indication of current intraocular pressure.

2. A method according to claim 1 wherein Step (A) comprises implanting the optical pressure sensor such that it is positioned substantially within the anterior chamber of the eye.

3. A method according to claim 1 wherein Step (A) comprises implanting the optical pressure sensor such that it is positioned substantially within the posterior chamber of the eye.

4. A method according to claim 1 wherein the native ophthalmic lens has been removed from the eye leaving at least a portion of the lens capsule intact and wherein Step (A) comprises implanting the optical pressure sensor such that it is positioned substantially' within at least a remaining portion of the lens capsule.

5. A method according to claim 1 wherein the optical pressure sensor is attached to a support that is configured to hold the optical pressure sensor at a substantially fixed position within the eye, and wherein Step (A) comprises implanting the optical pressure sensor and the support such that the optical pressure sensor is thereby held in a substantially fixed position within the eye.

6. A method according to claim 5 wherein Step (A) comprises implanting the optical pressure sensor and the support such that the optical pressure sensor is held in a substantially fixed position within the anterior chamber of the eye.

7. A method according to claim 5 wherein Step (A) comprises implanting the optical pressure sensor and the support such that the optical pressure sensor is held in a substantially fixed position within the posterior chamber of the eye.

8. A method according to claim 5 wherein the support comprises a lens that is adapted to perform a vision correcting function when implanted in the eye and wherein Step (A) comprises implanting the optical pressure sensor and the support in the eye such that i) the optical pressure sensor senses intraocular pressure and ii) the lens at least partially corrects the patient's vision.

9. A method according to claim 5 wherein the support comprises a shunt that is designed to drain aqueous humor in a manner that lowers intraocular pressure of the eye and wherein Step (A) comprises implanting the optical pressure sensor and the support in the eye such that i) that the optical pressure sensor senses intraocular pressure and ii) the shunt drains aqueous humor in a manner that lowers intraocular pressure.

10. A method according to claim 4 wherein the optical pressure sensor is embedded in or attached to a prosthetic lens, said prosthetic lens being implantable within at least a remaining portion of the lens capsule in place of the previously removed native lens.

11. A method according to claim 1 wherein Step (A) comprises positioning the optical pressure sensor in the eye such that, when light is passed from the light source in Step (C), the light will pass through the cornea of the eye and will strike and be reflected by the optical reflecting element cavity.

12. A method according to claim 1 further comprising the steps of:
   (E) implanting in the eye a optical analyte sensor having an optical reflecting element that varies in relation to the concentration or presence of at least one analyte;
   (F) using a light source to cast light into the eye such that the g will strike and be reflected by the optical reflecting element of the analyte sensor; and,
   (G) using a receiver/processor to receive light which has reflected from the optical reflecting element of the analyte sensor and Co process such reflected light so as to obtain a qualitative or quantitative determination of at least one analyte.

13. A method according to claim 12 wherein the optical pressure sensor and the analyte sensor are attached to a common support that holds both the optical pressure sensor and the analyte sensor at substantially fixed positions within the eye and wherein Steps (A) and (E) are performed concurrently by implanting the optical pressure sensor, analyte sensor and accompanying support within the eye.

14. A method according Co claim 12 wherein different light sources are used in Steps C and F.

15. A method according to claim 12 wherein the same light source is used in Steps C and F.

16. A method according to claim 15 wherein the wavelength of light emitted from the light source is variable and wherein a first wavelength is used in Step (C) and a second wavelength is used in Step (F).

17. A method according to claim 12 wherein different receiver/processors are used in Steps (D) and (G).

18. A method according to claim 12 wherein the same receiver/processor is used in Steps (D) and (G).

19. A method according to claim 18 wherein at least one setting on the receiver/processor is variable and wherein at least one first setting of the receiver/processor is used in Step (D) and at least one second setting of the receiver/processor is used in Step (G).

20. A method according to claim 12 wherein the analyte sensor is adapted to measure or to detect glucose and wherein Step (G) comprises obtaining a qualitative or quantitative determination of glucose.

21. A method according to claim 1 wherein the plurality of wavelengths comprise 820 nm, 850 nm and 880 nm.

* * * * *